United States Patent [19]
Solar et al.

[11] Patent Number: 6,042,553
[45] Date of Patent: Mar. 28, 2000

[54] LINEAR ELASTIC MEMBER

[75] Inventors: Matthew S. Solar, Cooper City; Eric Welch; Richard Acevedo, both of Miami, all of Fla.

[73] Assignee: Symbiosis Corporation, Miami, Fla.

[21] Appl. No.: 08/842,614

[22] Filed: Apr. 15, 1997

[51] Int. Cl.[7] ........................................ A61B 5/00
[52] U.S. Cl. ..................... 600/585; 604/95; 604/96; 604/280
[58] Field of Search ................. 600/585; 604/95, 604/96, 280, 281, 282

[56] References Cited

U.S. PATENT DOCUMENTS

| | | | |
|---|---|---|---|
| 4,579,127 | 4/1986 | Haacke | 600/585 |
| 5,007,434 | 4/1991 | Doyle et al. | 600/585 |

FOREIGN PATENT DOCUMENTS 0 340 304 A1   8/1989   European Pat. Off. .

Primary Examiner—Cary O'Connor
Assistant Examiner—Pamela Wingood
Attorney, Agent, or Firm—Todd P. Messal

[57] ABSTRACT

An elongate elastic metal alloy member for use in a medical device. The elongate member may be formed from a linear elastic metal alloy which may be twisted such that the torsional elasticity of the member is removed while the longitudinal flexibility of the member is maintained. The elongate member may further be placed under tension, fixed to prevent rotation, and heat treated such that the stress caused by tensioning and twisting the member is relieved without transforming the linear elastic metal alloy into a superelastic metal alloy. The resulting elongate elastic metal alloy member may have increased straightness and may be easier to grind.

8 Claims, 2 Drawing Sheets

LINEAR ELASTIC MEMBER

FIELD OF THE INVENTION

The present invention generally relates to improved processing methods for linear elastic alloys and applications of these alloys. General applications of these alloys may include medical wires and hypotubes. Specific applications of wires may include but are not limited to guide wires, pull wires in catheters and endoscopes, shafts for balloon catheters and cytology brushes, stents, braid within catheters and drive shafts for ultrasound or atherectomy/thrombectomy catheters. Specific applications of hypotubes may include but are not limited to guide wires, stents, needles, needle stylets, drive shafts and catheter components. Those skilled in the art will recognize the benefits of applying the present invention to similar fields not discussed herein.

BACKGROUND OF THE INVENTION

The term shape memory alloy (SMA) is applied to a group of metallic materials that demonstrate the ability to return to some previously defined shape or size when subjected to the appropriate thermal procedure. Generally, these materials can be plastically deformed at some relatively low temperature, and upon exposure to some higher temperature will return to their shape prior to the deformation. Materials that exhibit shape memory only upon heating are referred to as having a one-way shape memory. Some materials also undergo a change in shape upon re-cooling. These materials have a two-way shape memory. A relatively wide variety of alloys are known to exhibit the shape memory effect. They include:

| Alloy | Composition |
|---|---|
| AgCd | 44–49 at. % Cd |
| AuCd | 46.5–50 at. % Cd |
| CuAlNi | 14–14.5 wt. % Al |
|  | 3–4.5 wt. % Ni |
| CuSu | ~15 at. % Sn |
| CuZn | 38.5–41.5 wt. % Zn |
| CuZnX | a few wt. % X |
|  | X = Si, Sn, Al |
| InTi | 18–23 at. % Ti |
| NiAl | 36–38 at. % Al |
| NiTi | 49–51 at. % Ni |
| FePt | ~25 at. % Pt |
| MnCu | 5–35 at. % Cu |
| FeMnSi | 32 wt. % Mn |
|  | 6 wt. % Si |

To date only the nickel-titanium alloys (NiTi or Nitinol) and copper-base alloys such, as CuZnAl and CuAlNi, can recover enough strain or generate enough force upon changing shape to be of commercial interest.

Shape memory alloys may be characterized by several general methods including chemical, thermochemical, crystallographic, and stress/strain. Chemical analysis of a shape memory alloy may be further defined as an alloy that yields a thermoelastic martensite. In this case, the alloy undergoes a martensitic transformation of a type that allows the alloy to be deformed by a twinning mechanism below the transformation temperature. The deformation is then reversed when the twinned structure reverts upon heating to the parent phase.

Crystallographic analysis of a shape memory alloy shows a herringbone structure of athermal martensites essentially consisting of twin-related self-accommodating variants. The shape change among the variants tends to cause them to eliminate each other and, as a result, little macroscopic strain is generated. In the case of stress-induced martensites, or when stressing a self-accommodating structure, the variant that can transform and yield the greatest shape change in the direction of the applied stress is stabilized and becomes dominant. This process creates a macroscopic strain which is recoverable as the crystal structure reverts to austenite during reverse transformation.

In addition to their ability to return to some previously defined shape or size when subjected to an appropriate thermal procedure, shape memory alloys also have the useful mechanical characteristic of being highly elastic or super-elastic. Super-elastic metals can appear to be stressed beyond their elastic yield point but still return to their original shape after the stress is removed. As can be seen from the stress-strain diagram of FIG. 1, a super-elastic metal that is stressed has a first portion Q where the stress and the strain are proportional. The diagram further shows the classic flagged shaped curve of a superelastic alloy with the transition point X marking the beginning of plateau P where the metal continues to elongate while the stress is unchanged. Finally, if the stress is removed, the alloy will return to its original shape without any plastic deformation. Super-elastic alloys are then able to take more of a load without permanent deformation than conventional metals.

Elastic metals or super-elastic precursors may also be shape-memory alloys but elastic metals do not have the stress-strain plateau of a super-elastic alloy. FIG. 2 is a stress-strain diagram of an elastic metal which again shows a proportional region Q. Similar to conventional metals, an elastic metal would break if stressed much beyond its yield point Y. However, unlike a conventional metal, an elastic metal will take much more strain than conventional metals before yielding. Elastic metals then are able to take a large load with only a small amount of permanent deformation and are generally stiffer than super-elastic metals.

To date NiTi shape memory alloys have been the most commercially successful. Processing of NiTi shape memory alloys include selective work hardening, which can exceed 50% reduction in some cases. Proper heat treatment can also greatly improve the ease with which the martensite is deformed, give an austenite with much greater strength, and create material that spontaneously moves itself both on heating and on cooling (two-way shape memory). One of the biggest challenges in using this family of alloys is in developing the proper processing procedures to yield the properties desired.

Because of the reactivity of the titanium in these alloys, all melting of them must be done in a vacuum or an inert atmosphere. Methods such as plasma-arc melting, electron-beam melting, and vacuum-induction melting are all used commercially. After ingots are melted, standard hot-forming processes such as forging, bar rolling, and extrusion can be used for initial breakdown. The alloys react slowly with air, so hot working in air is quite successful. Most cold-working processes can also be applied to these alloys, but they work harden extremely rapidly, and frequent annealing is required. Wire drawing is probably the most widely used of the techniques, and excellent surface properties and sizes as small as 0.05 mm (0.002 in.) are made routinely. Super-elastic wires have a relatively high kink resistance but lack both axial and torsional stiffness. Linear elastic wires have slightly lower kink resistance than super-elastic wires but higher torsional rigidity. Unfortunately, elastic wires also are very difficult to keep straight during processing.

Fabrication of articles from the NiTi alloys can usually be done with care, but some of the normal processes are difficult. Machining by turning or milling is very difficult except with special tools and practices. Welding, brazing, or soldering the alloys is also generally difficult. Heat treating to impart the desired memory shape is often done at 500 to 800° C. (950 to 1450° F.). The SMA component may need to be restrained in the desired memory shape during the heat treatment; otherwise, it may not remain there.

The most common medical use of these materials to date is as core wires in guide wires. Guide wires are used in minimally invasive medical procedures. Typically, a guide wire is inserted into an access point and then advanced through a body lumen, such as a blood vessel, to a site to be treated. Another medical device that actually performs the treatment is then advanced over the guide wire.

A typical guide wire 20 is shown in FIG. 3. Guide wire 20 has a core 25 and a polymer sleeve 10. Best performance in guide wire cores is based on a combination of factors which include a small diameter, smooth finish, straightness, pushability, kink resistance, and torqueability. The diameter of the wire core ultimately determines the diameter of the lumen that can be treated. For example, in the neurovasculature where the vessels may be extremely small, having a small diameter wire core is very important.

The finish of a guide wire often affects the performance of therapeutic devices that are slid over the wire since a rough surface will increase the drag on any device. Surface friction may be reduced by polishing or through the use of lubricious coatings. Similarly, it is important that the wire core and ultimately the guide wire be as straight as possible to reduce the number of points where the guide wire contacts the therapeutic device. Wire cores may be mechanically straightened or ground to remove uneven surfaces.

Pushability, kink resistance, and torqueability are closely related and important features of a guidewire. It is important that force applied at the proximal end of the guide wire is completely transferred to the distal end of the guide wire. Very stiff wire cores often provide good pushability (axial rigidity) but poor kink resistance. Kink resistance is measured by the ability of the guide wire to be forced into a relatively tight bend radius without permanently deforming the wire core. Finally, torqueability is closely related to the torsional rigidity of the wire core. That is, how well rotation imparted to the proximal end of the guide wire is translated to the distal end of the guide wire.

Conventional guide wire cores are made of carbon steel or stainless steel. More recently, guide wire cores made of super-elastic alloys have been used. A super-elastic or pseudoelastic metal guide wire core was taught in U.S. Pat. No. 4,925,445 to Sakamoto. In U.S. Pat. Nos. 5,238,004 to Sahatian and U.S. Pat. No. 5,230,348 to Ishibe the use of an elastic metal alloy was taught. Sahatian '004 further teaches that elastic metals may be heat treated to form bends in the wire core and that centerless grinding may be used to create certain wire core profiles.

It is well known in the art to centerless grind guide wire cores to provide desired core profiles. Generally, centerless grinders are used to grind the outer surface of the wire core. The object of the grinding operation is to produce a wire core that is round, straight and has a diameter and surface finish in accordance with given specifications at any given cross-section along its length.

Typically, a wire core is fed into a centerless grinder at one end and guided between two grinding wheels that rotate in the same direction at different speeds, known as the work wheel and the regulating wheel. The wire core rotates as a result of its contact with the regulating wheel and is ground to a specified diameter dictated by the distance between the faces of the two grinding wheels. One of the grinding wheels, typically the regulating wheel, can be moved so that the distance between the faces of the grinding wheels may be varied during the grinding process. The wire core advances through the grinding machine as a result of its contact with the grinding wheels. Specifically, one of the grinding wheels, typically the regulating wheel, rotates along an axis that is almost parallel to the axis of rotation of the wire core being ground, but slightly skewed in a vertical plane, so that its contact with the wire causes the wire to move forward through the machine.

A number of factors can affect the rate at which the wire moves through the grinding machine and the rate at which wheels must be changed. For example, temperature, regulating wheel RPM, regulating wheel tilt angle, slippage, type of coolant used, and grinding wheel material may affect feed rate, wire core diameter, wire core material, and wire core uniformity. As may be appreciated from the description of the centerless grinding process, having a straight and preferably uniform wire is essential to effective centerless grinding.

As previously described, a typical linear elastic wire is not straight and is, in fact, roughly sinusoidal following the typical processing regime. As can be seen in FIG. 3, it is desirable to grind a taper 15 into the distal end of the guide wire core to make the wire more flexible near its distal tip. Attempts to grind linear elastic wire cores have proven to be destructive to the grinding equipment since the wire core is not straight and is relatively stiff. It is therefore desirable to provide a linear elastic wire for use as a guide wire core which is straight enough to be easily ground to a desired shape.

In addition to guide wires, many other devices may benefit from the characteristics of a linear elastic elongate member. General applications of elastic alloys may include medical wires and hypotubes. Specific applications of wires may include but are not limited to guide wires, pull wires in catheters and endoscopes, wire stents and drive shafts for ultrasound or atherectomy/thrombectomy catheters. Specific applications of hypotubes may include but are not limited to guide wires, stents, needles, needle stylets, drive shafts and catheter components. It may therefore be desirable to provide a linear elastic wire or hypotube which is easily ground to a desired shape and to use that wire or hypotube in any of the applications described above.

In U.S. Pat. No. 4,445,509 to Auth a rotary atherectomy device is taught. This device essential consists of a catheter with a bur located on the distal end. Within the catheter is a drive shaft which rotates the bur at high speed, greater than 20,000 RPM. The proximal end of the drive shaft is connected to a motor which powers the entire assembly.

Another common drive shaft application is in ultrasound catheters. In U.S. Pat. No. 4,794,931 to Yock a flexible drive shaft connects a proximal power source outside the body, through a catheter, to a distal ultrasonic transducer. The transducer is rotated and provides an ultrasonographic image of the interior of a body lumen. In this and other well known drive shaft applications the shaft must be flexible, have high kink resistance, and excellent torsional rigidity.

Small tubes or hypotubes are also commonly used in the medical device industry. In some applications like drive shafts and guide wires, hypotubes perform a similar function to wires but also have the advantage of a hollow space to perform some other action. As an example U.S. Pat. No. 4,953,553 to Tremulis teaches a hypotube used as a guide wire which may further be used to measure pressure insitu or to infuse liquids. Needle stylets are similar to guide wires in that they are advanced through other medical devices. Stylets are commonly used to add support to the medical device that is slid over it.

Another application for medical hypotubes is in catheter shafts. Examples of such catheters include but are not limited to catheters for angiography or catheters for dilating blood vessels. Angiography catheters typically have a main body formed of a somewhat soft thermoplastic resin and a rigidity imparting member consisting of a metallic braided wire (generally a stainless-steel wire). The rigidity imparting member is disposed around the main body such that kinking of the catheter is inhibited while its high flexibility is maintained. The rigidity imparting member further improves the torque transmission efficiency.

Design of balloon catheters is similar with the addition of a distal inflatable member for dilating a stenosis portion in a blood vessel. These catheters often comprise an inner tube made of a flexible polymer, an outer tube made of a flexible polymer and disposed coaxially with the inner tube, and a balloon attached to the outer tube at the balloon's proximal end and attached to the inner tube at the balloon's distal end. The inner or outer tube may be provided with a rigidity imparting member consisting of a metallic wire braid (e.g., a stainless-steel wire).

The rigidity imparting member used in the above catheters can inhibit kinking and improve torque transmission efficiency to some extent. Rigidity, pushability, and torque transmission were further improved by Peters et al. in U.S. Pat. No. 5,549,552 which teaches the use of a super-elastic metal hypotube as the rigidity imparting member described above.

Yet another application of super-elastic metal hypotubes is in stents. It is well known in the art to make stents of Nitinol. These stents are often made by laser cutting a Nitinol hypotube and then further processing the cut stent depending on specific applications or desired geometries.

In each of the applications previously described and in many other related applications it is therefore desirable to provide a metal alloy which is flexible, axially and torsionally rigid, kink resistant and straight.

SUMMARY OF THE INVENTION

The present invention improves upon the prior art by providing improved elastic metal wires or tubes which are torsionally more rigid than super-elastic metal wires or tubes and straighter and easier to process than conventional elastic metal wires or tubes. These improved elastic metal wires or tubes are made by twisting the wire or tube, putting the elastic metal wire or tube under tension, and then fixing the wire or tube such that it can not rotate. While the wire or tube is fixed, at least a portion of the wire or tube may be heat treated to increase the torsional rigidity by removing some of the torsional elasticity while maintaining longitudinal flexibility. Heat treatment may be done at a temperature that is low enough not to affect the linear properties of the metal. Wires or tubes processed in this manner may be used in a variety of medical devices including but not limited to guide wires, stents, needles, needle stylets, catheter drive shafts, pull wires for catheters or endoscopes, shafts for cytology brushes, and stiffening members within catheters.

DETAILED DESCRIPTION OF THE INVENTION

Figure 1:
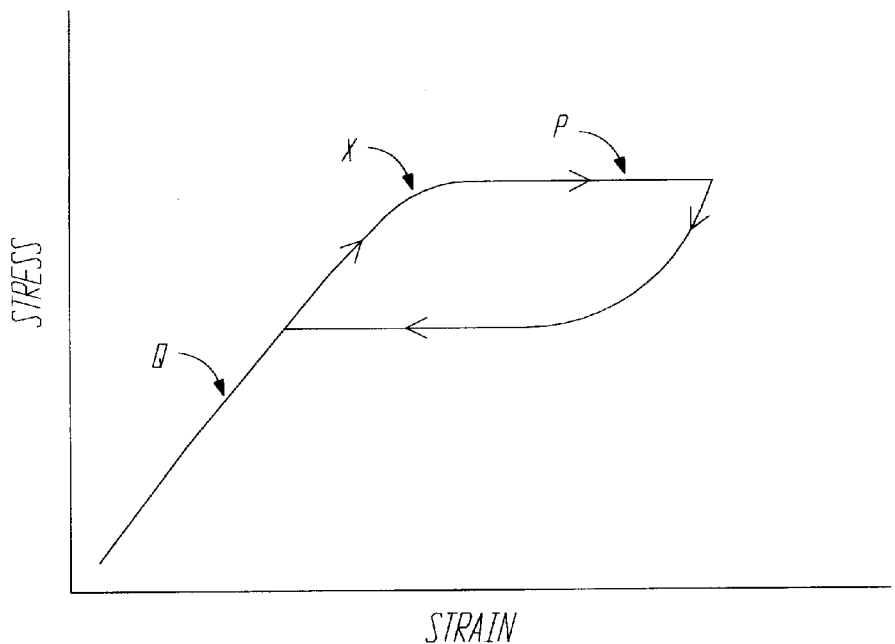
FIG. 1 is a stress strain diagram for a super-elastic alloy metal.
Figure 2:
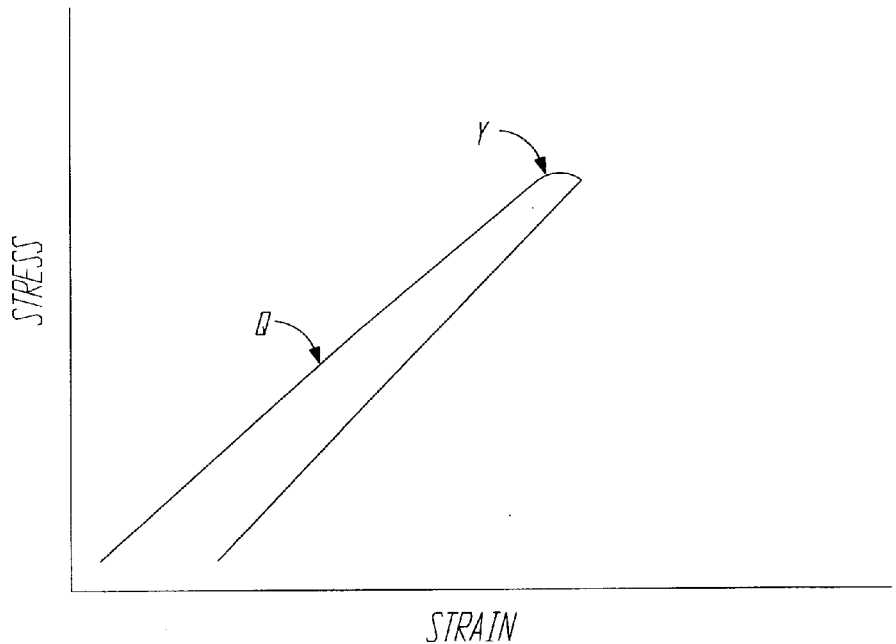
FIG. 2 is a stress strain diagram for a linear elastic alloy metal.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

The process of producing straight linear elastic wire or tubing begins with forming an alloy of about 49–51% nickel and about 49–51% titanium and then drawing it down into the desired shape. The drawing process typically adds a significant amount of cold work and should be done such that 20–45% cold work is induced into the wire or tubing. Preferably a nickel-titanium alloy such as NDC:SE 508 wire core, provided by Nitinol Devices & Components, Inc. of Fremont, Calif., with about 35% cold work added may be used. After drawing, the wire or tube is in its elastic form. However, as such, the wire or tubing also is not straight.

All or a portion of the wire or tube may be twisted. Twisting the wire or tube helps increase torsional rigidity by removing some of the torsional elasticity while maintaining longitudinal flexibility. Care must be taken not to add so many turns to the wire or tube that additional cold work is done and thereby undesirably increase the hardness of the wire or tube. Those skilled in the art may recognize that the number of turns per foot of wire or tube may vary depending on the size or material characteristics of the wire or tube.

The wire or tube should next be placed under tension. The tension may vary depending on the diameter of the wire or the wall thickness of the tube and the preferred amount of tension may be greater for larger diameter wire or larger wall thickness tubing. In addition to placing the wire or tube under tension the wire or tube must be prevented from untwisting. While separate fixtures may be used to hold the wire or tube under tension and to prevent it from rotating, a preferred method of manufacture may be to use a single fixture to keep the wire or tube under tension and simultaneously prevent rotation. This fixture may be suitable for batch processing individual wire or tubes or for inline processing of wire or tube stock. Other material properties may also affect the wire or tube and those skilled in the art will recognize that excess tension may adversely affect the material properties of a wire or tube and that care should be taken to limit tension on the wire or tube such that further cold work is not done.

While wire or tube is under tension and prevented from rotating the wire or tube is heat treated. Heat treating may be done in a furnace, with resistance heating, or any other way commonly known in the art. The wire or tube may be heated as high as about 400° C. However, care must be taken not to heat treat the wire or tube at elevated temperatures because the linear elastic alloy may be transformed into a super-elastic alloy. In order to avoid transforming the elastic alloy into a super-elastic alloy, it is preferred that the wire or tube be heated to about 280–300° C.

The amount of time that the wire or tube stays at temperature may be as little as a few minutes but must be sufficient to relax the stress caused by the tensioning and twisting process. Simply bringing the wire or tube to the preferred temperature and then allowing it to cool may be enough to adequately straighten the wire or tube. Preferably the wire or tube may be heat treated at 280–300° C. for about 30 minutes. Those skilled in the art will recognize that the temperature and amount of time that the wire or tube is kept at that temperature may vary depending upon the diameter, wall thickness, or other material characteristics of the wire or tube but that the time and temperature should remain consistent with the goals of having a straight linear elastic wire or tube.

Each of the previously described processing steps may be applied to all or a portion or portions of the wire or tubing. In addition, portions of the wire or tubing may be processed to different degrees and thereby provide different degrees of flexibility, axial and torsional rigidity, or straightness along the wire or tubing. The processing steps may also be applied to the wire or tubing in batches or on a continuous basis.

Figure 3:
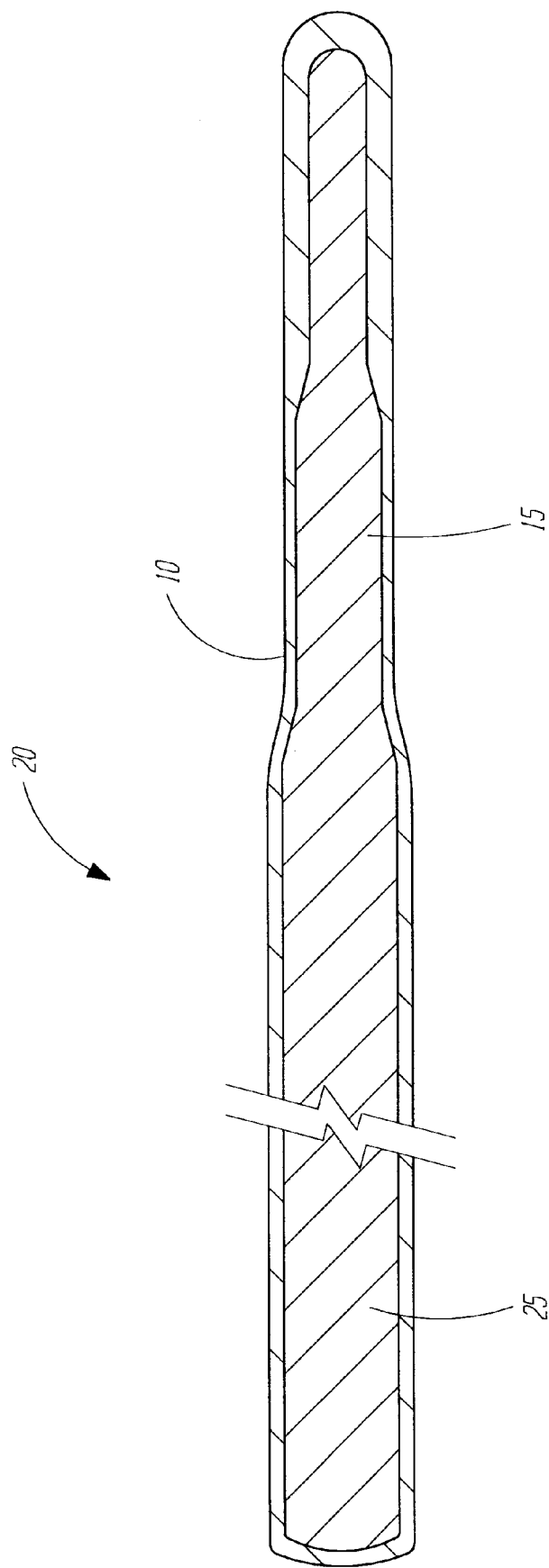
FIG. 3 is cross section of a guide wire.

The following is one example of application of the straightening process to a linear elastic wire for a guide wire core. Referring now to FIG. 3, an 0.018 inch guide wire 20 is shown. Guide wire 20 may have a core wire 25 over most of its length with a gradual taper 15 near the distal end of core wire 25. Taper 15 makes the distal end of guide wire 20 more flexible. Alternatively, a spring coil (not shown) may be attached to the distal end of guide wire 20 for added flexibility. One or more flexible sleeves 10 may be closely fitted to and covers the core wire 25 over a portion or the entire length of core wire 25. The flexible sleeve 10 may be made of hydrophilic or other lubricious polymers. The flexible sleeve 10 may further be marked with stripes for endoscopic viewing. Alternatively, fluoroscopic viewing may be aided by incorporating a radio-opaque stripe into sleeve 10. The preceding discussion is descriptive of guide wires as are commonly known in the art. More detail on various guide wire embodiments and methods of construction may be found in U.S. Pat. No. 5,379,799 to Rowland which is hereby incorporated by reference.

The preceding processing steps may be advantageously applied to guide wire cores and the following preferred processing parameters are for a guide wire diameter of 0.018 inches. As previously described, a work hardenend NiTi alloy wire with about 20–45% cold work added may be twisted with as many as 30 turns per foot and preferably about 15 turns per foot. After twisting, the wire may be placed under tension and the wire may further be fixed to prevent rotation. As little as 1 pound of tension may be used. However, it is preferred that about 2 pounds of tension be applied. Heat treatment may next be done at temperatures of about 280–300° C. with the wire held at that temperature for about 30 minutes. Those skilled in the art will recognize that the amount of twist, amount of tension, temperature and length of heat treatment may vary depending upon the diameter and other material characteristics of the wire but that processing parameters should remain consistent with the goals of having a straight linear elastic wire core.

After the wire core has been heat treated it will be straighter than an untreated wire core and therefore easier to process. The core wire 25 may then be ground such that a distal taper 15 is made in the distal end. Additional details on various wire core centerless grinding techniques may be found in U.S. Pat. No. 5,480,342 to Bannayan which is herein incorporated by reference. The core wire 25 may then be covered with one or more flexible sleeves 10 to complete the construction.

As previously described elastic metal alloy wires or tubes may be useful in variety of other medical applications if the wires or tubes are straight. Therefore the previously described processing steps for a linear elastic alloy may be used in, or to create new applications of elastic metal wires and tubes in medical devices. Variations in the processing steps described above may be made as necessary depending upon the diameter of the wire and any other desired characteristics as appropriate to the application.

Pull wires are commonly used in medical devices where motion is desired at a distant region of a device. Examples of these devices include endoscopes, electrophysiology catheters, biopsy devices, and other special application catheters. Wires within these devices need to have high kink resistance and good torsional rigidity. These wires further need to be straight to reduce frictional loss due to contact between the device and the wire and thereby provide a greater mechanical advantage at the distal end of the device. As such, elastic metal alloys as previously described may be advantageously used for pull wires.

Stents are also well known to the medical arts and are used to hold open body lumens. Common lumens where stents are used include the vasculature, the biliary tract, and the urinary tract. Many types and geometries of stents are also taught by the prior art including wire stents and stents formed from tubes. Wire stents are usually woven to form a cage-like tubular structure or tubes are cut to form a tubular structure. Because of their strength and flexibility, elastic metal alloys are often preferred. Since the exterior of the stent holds open the body lumen, it is advantageous to have as much of the stent as possible in contact with the vessel wall. Straighter wires or tubes may provide more contact between the stent and the vessel wall and more support. Therefore elastic alloy wires or tubes which have been straightened as previously described would be advantageous.

Wire braid is another well known addition to medical devices. Braid is incorporated into guide catheters, balloon catheters, angiography catheters, and other specialty devices. Further details of construction of catheters incorporating wire braid are described in U.S. Pat. No. 5,338,295 to Cornelius which is herein incorporated by reference. Typically a tubular wire braid is woven into or bonded to the catheter body to provide increased pushability, provide greater kink resistance, and give higher crush strength. As such, straighter elastic alloy wires processed as described above may be used to form braid in any of the previously described devices.

Hypotubes are also well known components of catheter shafts. Similar to braid as described above, hypotubes should be pushable, have kink resistance, transmit torque well and have higher crush strength. Hypotubes should further be straight and uniform in shape. In addition hypotubes are often ground on their distal ends to create a change of flexibility in a catheter or to create a good bonding region. Further details of construction of catheters using hypotubes are described in U.S. Pat. No. 5,549,552 to Peters et al. which is herein incorporated by reference. Catheters or guide wires using hypotubes made with an elastic alloy that is straightened as described above would be beneficial.

Cytology devices, as is well known in the art, are used to take cell samples from places within the body that are not readily accessible by other biopsy devices. Typically a cytology device consists of a bristled brush which is rubbed against a particular part of the body. The bristles remove cells and trap them for subsequent analysis. The process of moving the cytology brush back and forth may best be performed with a kink resistant shaft and the process of rubbing the bristles against a sample site further requires enhanced torsional rigidity. Similar to other catheters previously described, elastic metal hypotubes or wires processed as previously described may be used to provide improved shaft performance in a cytology device.

Comfort in needles is a function of the sharpness and straightness of the needle. Needles are essentially made of hypotubes which have their distal end cut at an angle. Needles may then be made of a linear elastic alloy which has been processed as described above. The needle may then be straighter than conventional needles and hence more comfortable to the user. In addition, the distal end of the needle may be more easily ground to a sharp edge and again be more comfortable to the user. Similar to needles, needle stylets may also be made of an elastic metal alloy processed as previously described.

Drive shafts are important components in atherectomy/thrombectomy catheters and ultrasound imaging catheters. In each type of catheter a long flexible drive shaft runs the length of the catheter and transfers rotational energy from the proximal end of the catheter to the working element at the distal end of the catheter. In atherectomy/thrombectomy catheters the working element is usually some sort of cutter. Further details of atherectomy/thrombectomy catheters are described in U.S. Pat. No. 4,445,509 to Auth which is herein incorporated by reference. It is important to note that the cutter taught by Auth '509 rotates at over 20,000 RPM and therefore the drive shaft needs to be flexible, have good kink resistance, and excellent torsional rigidity. Similarly, the working element in ultrasound imaging catheters is an ultrasonic transducer which is rotated at the distal end of a catheter.

Prior art drive shafts have been made of a wire or a number of wires twisted together. Drive shafts may then be made of an elastic metal alloy processed as previously described to provide improved torsional rigidity and straighter wires. Additionally, hypotubing may be used as a drive shaft. It is critical when using hypotubing for a drive shaft that the hypotube be as straight as possible and that the wall thickness be as uniform as possible. Hypotubes which are not straight or are non-concentric cause extreme vibration at high speeds resulting in poor performance for atherectomy/thrombectomy catheters and non-uniform rotational distortion in ultrasound imaging catheters. In both applications the performance of these catheters may be improved by providing drive shaft hypotubing made of an elastic metal processed as previously described.

While the specification describes the preferred designs, materials, methods of manufacture and methods of use, those skilled in the art will appreciate the scope and spirit of the invention with reference to the appended claims.

We claim:

1. A guide wire core for use in a guide wire comprising:

an elongate member formed by twisting an elongate linear elastic shape memory metal alloy member such that torsional elasticity is removed while longitudinal flexibility is maintained, placing the elongate member under tension, fixing the elongate member such that the elongate member remains twisted, and heat treating at least a portion of the elongate member such that stress caused by tensioning and twisting is relieved without transforming the elongate member into a super-elastic alloy; and an end portion of the elongate member formed by grinding an end of the elongate member to increase the flexibility of the end of the elongate member.

2. The guide wire core of claim 1 wherein the linear elastic shape memory metal alloy comprises about 50% nickel and about 50% titanium.

3. The guide wire core of claim 1 wherein the step of twisting the elongate member comprises up to 30 turns per linear foot.

4. The guide wire core of claim 3 wherein the step of twisting the elongate member comprises about 15 turns per linear foot.

5. The guide wire core of claim 1 wherein the elongate member is 20–45% cold worked prior to twisting.

6. The guide wire core of claim 1 wherein the step of placing the elongate member under tension is done with about 2 pounds of tension.

7. The guide wire core of claim 1 wherein the step of heat treating is performed at a temperature of less than about 400 degrees C.

8. The guide wire core of claim 7 wherein the step of heat treating is performed at about 280–300° C. for about 30 minutes.

* * * * *